(12) United States Patent
Yang et al.

(10) Patent No.: US 7,501,510 B2
(45) Date of Patent: Mar. 10, 2009

(54) THIOUREA COMPOSITIONS AND USES THEREOF

(75) Inventors: Dan Yang, Hong Kong (HK); Ying-Chun Chen, Chengdu (CN)

(73) Assignee: The University of Hong Kong, Hong Kong (CN)

(*) Notice: Subject to any disclaimer, the term of this patent is extended or adjusted under 35 U.S.C. 154(b) by 455 days.

(21) Appl. No.: 11/089,197

(22) Filed: Mar. 24, 2005

(65) Prior Publication Data

US 2005/0215783 A1   Sep. 29, 2005

Related U.S. Application Data

(60) Provisional application No. 60/556,570, filed on Mar. 26, 2004.

(51) Int. Cl.
*C07D 487/00* (2006.01)
*C07D 403/02* (2006.01)

(52) U.S. Cl. .................... 540/495; 548/312.7

(58) Field of Classification Search ............... 540/495; 548/312.7
See application file for complete search history.

(56) References Cited

OTHER PUBLICATIONS

Cattalani et al. Gazzetta Chimica Italiana (1988), 118(10), 725-8 CODEN: GCITA9; ISSN: 0016-5603. (CAS Abstract Only).*
Atzordt et al. Tetrahedron: Asymmetry vol. 8, Issue 13, Jul. 10, 1997, pp. 2257-2260.*
Hassan, J. et al., "Aryl-Aryl Bond Formation One Century after the Discovery of the Ullmann Reaction," Chem. Rev. 2002, 1359-1469, vol. 102.
Darses, S. and Genet, J., "Potassium Trifluoro(organo)borates: New Perspectives in Organic Chemistry," Eur. J. Org. Chem., 2003, 4313-4327.
Molander, G. et al., "Development of the Suzuki-Miyaura Cross-Coupling Reaction,"J. Org. Chem., 2002, 8416-8423, vol 67, American Chemical Society.
Darses, S. et al., "Potassium Organotrifluoroborates: New Partners in Palladium-Catalysed Cross-Coupling Reactions," Eur. J. Org. Chem., 1999, 1875-1883.
Miura, M., "Rational Ligand Design in Constructing Efficient Catalyst Systems for Suzuki-Miyaura Coupling," Angew. Chem. Int. Ed., 2004, 2201-2203, vol. 43.
Davis, Jr., J. and Fox, P.A., "From Curiosities to Commodities: Ionic Liquids Begin the Transition," Chem. Commun., 2003, 1209-1212, The Royal Society of Chemistry.
Dupont, J. et al., "Ionic Liquid (Molten Salt) Phase Organometallic Catalysis," Chem. Rev., 2002, 3667-3692, American Chemical Society.
Olivier-Bourbigou, H. and Magna, L., "Ionic Liquids: Perspectives for Organic and Catalytic Reactions," J. Mol. Catalysis, 2002, 419-437, Elsevier Science.
Kumaravel, S. et al., "New Palladium Carbene Catalysts for the Heck Reaction of Aryl Chlorides in Ionic Liquids," Organic Letters, 2002, 3031-3033, vol 4, No. 18.

Gurtler, C. and Buchwald, S.L., "A Phosphane-Free Catalysts System for the Heck Arylation of Disubstituted Alkenes," Chem. Eur. J., 1999, 3107-3112, vol. 5, No. 11.
Dai, M. et al., "Synthesis of a Novel C2-Symmetric Thiourea and Its Application in the Pd-Catalyzed Cross-Coupling Reactions . . . ," Organic Letters, 2004, 221-224, vol. 6, No. 2.
Hu, Y. and Yang, Z., "Palladium-Mediated Intramolecular Carbonylative Annulation of o-Alkynylphenols . . . ," Organic Letters, 2001, 1387-1390, vol. 3, No. 9.
Miao, H. and Yang, Z., "Regiospecific Carbonylative Annulation of Iodophenol Acetates and Acetylenes . . . ," Organic Letters, 2000, 1765-1768, vol. 2, No. 12.
Nan, Y. et al., "A New Complex of Palladium-Thiourea and Carbon Tetrabromide Catalyzed . . . ," Organic Letters, 2000, 297-299, vol. 2, No. 3.
Zhang, T. and Allen, M., "An Easily Prepared, Air and Moisture Stable, Resin-bound Palladium Catalyst for Suzuki . . . ," Tetrahedron Letters 40, 1999, 5813-5816.
Bartolo, G. et al., "Combined Oxidative and Reductive Carbonylation of Terminal Alkynes . . . ," Journal of Organometallic Chemistry, 1995, 21-28, 503.
De Munno, G. et al., "X-ray Structure of Palladium (II) Tetrakis-Thiourea Iodide, a Catalyst for Carbonylation Reactions," Inorganica Chimica Acta, 1995, 181-183, 234.
Touchard, F. et al., "Ureas and Thioureas as Rh-Ligands for the Enantioselective Hydride Transfer Reduction of Acetophenone," Journal of Molecular Catalysis, 1999, 1-11.
Breuzard, J. et al., "Thioureas as New Chiral Ligands for the Asymmetric Hydroformylation of Styrene . . . ," Journal of Molecular Catalysis, 2000, 223-232.
Tommasino, M. et al., "Asymmetric Hydrogenation of Enamides with Catalysts Containing Chiral Thiourea Ligands," Tetrahedron: Asymmetry 11, 2000, 4835-4841.
Touchard, F. et al., "Optically Active Nitrogen Ligands in Asymmetric Catalysis. Effect of Nitrogen . . . ," Journal of Organometallic Chemistry, 1998, 133-136, 567.
Touchard, F. et al., "Chiral Thiourea as Ligand for the Asymmetric Reduction of Prochiral Ketones," Tetrahedron Letters, 1997, 2275-2278, vol. 38, No. 13.
Touchard, F. et al., "Thioures: New Ligands for the Metal Catalyzed Asymmetric Reduction . . . ," Tetrahedron: Asymmetry, 1997, 3319-3326, vol. 8, No. 19, Pergamon.
Masllorens, J. et al., "First Heck Reaction with Arenediazonium Cations with Recovery of Pd-Triolefinic Macrocyclic Catalyst," Organic Letters, 2003, 1559-1561, vol, vol. 5, No. 9.

(Continued)

*Primary Examiner*—Kamal A Saeed
(74) *Attorney, Agent, or Firm*—Robert D. Katz; Cooper & Dunham LLP

(57) ABSTRACT

The invention provides N,N'-disubstituted monothiourea or bis-thiourea-Pd(0) complexes that are useful as catalysts for palladium-catalyzed Heck reaction of aryl iodides and bromides with olefins, and as catalysts for palladium catalyzed Suzuki reactions of organoboric compounds and aryl halides.

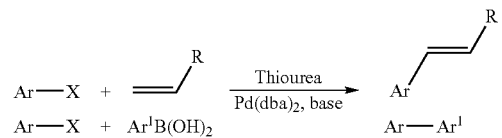

8 Claims, 2 Drawing Sheets

OTHER PUBLICATIONS

Silberg, J. et al., "N-Acyl-N, N-Dipyridyl and N-Acyl-N-Pyridyl-N-Quinoyl Amine Based Palladium Complexes. . . . ," Journal of Organometallic Chemistry, 2001, 6-18.

Buchmeiser, M. and Wurst, K., "Access to Well-Defined Heterogeneous Catalytic Systems via Ring-Opening Metathesis . . . ," J. Am. Chem. Soc., 1999, 11101-11107, 121.

Herrmann, W., "N-Heterocyclic Carbenes: A New Concept in Organometallic Catalysis," Angew. Chem. Int. Ed., 2002, 1291-1309, vol. 41, Wiley-VCH.

Reetz, M. et al., "A New Catalyst System for the Heck Reaction of Unreactive Aryl Halides," Angew. Chem. Int. Ed., 1998, 481-483, vol. 37, No. 4, Wiley-VCH.

Bedford, R., "Palladacyclic Catalysts in C-C and C-Heteroatom Bond-Forming Reactions," Chem. Commun. 2003, 1787-1796, University of Exeter.

Dupont, J. et al., "Palladacycles—An Old Organometallic Family Revisited: New, Simple, and Efficient Catalysts . . . ," Eur. J. Inorg. Chem., 2001, 1917-1927.

Shaw, B. and Perera, S., "Chelating Diphosphine-Palladium(II) Dihalides; Outstandingly Good Catalysts for Heck . . . ," Chem. Commun., 1998, 1863-1864.

Portnoy, M. et al., "Reactions of Electron-Rich Arylpalladium Complexes with Olefin. Origin of the Chelate Effect . . . ," Organometallics, 1994, 3465-3479, vol. 13.

Portnoy, M. and Milstein, D., "Chelate Effect on the Structure and Reactivity of Electron-Rich Palladium . . . ," Organometallics, 1993, 1655-1664, vol. 12.

Ben-David, Y. et al., "Palladium-Catalyzed Vinylation of Aryl Chlorides. Chelate Effect in Catalysis," Organometallics, 1992, 1995-1996, vol. 11.

Ehrentraut, A. et al., "A New Efficient Palladium Catalysts for Heck Reactions of Deactivated Aryl Chlorides," Synlett, 2000, 1589-1592, No. 11.

Shaughnessy, K. et al., "A Fluorescence-Based Assay for High-Throughput Screening of Coupling Reactions. Application to Heck Chemistry," J. Am. Chem. Soc., 1999, 2123-2132.

Littke, A. and Fu, G., "A Versatile Catalyst for Heck Reactions of Aryl Chlorides and Aryl Bromides under Mild Conditions," J. Am. Chem. Soc., 2001, 6989-7000, vol 123.

Littke, A. and Fu, G., "Heck Reactions in the Presence of P(t-Bu)3: Expanded Scope and Milder Reaction Conditions . . . ," J. Org. Chem., 1999, 10-11, vol. 64.

Whitcombe, N. et al., "Advances in the Heck Chemistry of Aryl Bromides and Chlorides," Tetrahedron, 2001,m 7449-7476, vol. 57, Elsevier Science Ltd.

Dounay, A. and Overman, L., "The Asymmetric Intramolecular Heck Reaction in Natural Product Total Synthesis," Chem. Rev., 2003, 2945-2963, vol. 103.

Beletskaya, I. and Cheprakov, A., "The Heck Reaction as a Sharpening Stone of Palladium Catalysis," Chem. Rev., 2000, 3009-3066, vol. 100, American Chemical Society.

Crisp, G., "Variations on a Theme—Recent Developments on the Mechanism of the Heck Reaction . . . ," Chemical Society Reviews, 1998, 427-436, vol. 27.

Cabri, W. and Candiani, I., "Recent Developments and New Perspectives in the Heck Reaction," Acc. Chem. Res., 1995, 2-7, vol. 28, American Chemical Society.

Heck, R., "Palladium-Catalyzed Reactions of Organic Halides with Olefins," Accounts of Chemical Research, 1979, 146-151, American Chemical Society.

Negishi, E. et al., "Cyclic Carbopalladation. A Versatile Synthetic Methodology for the Construction of Cyclic Organic Compounds," Chem. Rev., 1996, 365-393, vol. 96.

* cited by examiner

1a: R=H
1b: R=2,4,6-mesityl

1c

1j

1d: R=H
1e: R=Me
1f: R=4-MeO-Ph
1g: R=Mesityl
1h: R=2,6-Et$_2$-Ph
1i: R=2,5-Bu$^t_2$-Ph

1k

1l  1m  1n

1o  1p  1q

Cis- PdCl$_2$·(1g)$_2$

Trans- PdCl$_2$·(1g)$_2$

THIOUREA COMPOSITIONS AND USES THEREOF

This application claims priority of provisional application U.S. Ser. No. 60/556,570, filed Mar. 26, 2004, the contents of which are being incorporated herein by reference.

FIELD OF THE INVENTION

This invention relates to thiourea ligands and more particularly to thiourea-palladium complexes useful as catalysts for palladium catalyzed arylation of alkenes in a chemical reaction known as the Heck reaction, and as catalysts for palladium catalyzed Suzuki reactions of organoboric compounds and aryl halides.

BACKGROUND OF THE INVENTION

The palladium catalyzed arylation of olefins (the Heck reaction) is one of the most versatile tools for C—C bond formation in organic synthesis.[1] Phosphine ligands are generally used to stabilize the reactive palladium intermediates, and excellent results have been reported for Pd-catalyzed Heck reactions when sterically bulky mono-phosphines, diphosphines, cyclometalated phosphines, or phosphites are used as the ligands.[2-5] The air-sensitivity of phosphine ligands, however, places significant limits on their synthetic applications. Therefore, the development of phosphine-free palladium catalysts is a topic of enormous interest.[6-8] Thioureas are air and moisture stable solids and have recently been employed as ligands in Ru—, Rh—, or Pd-catalyzed reactions.[9-10] Very recently, Z. Yang[11] and coworkers reported the Heck and Suzuki reactions of highly active arenediazonium salts catalyzed by a chiral thiourea-Pd complex.

SUMMARY OF THE INVENTION

The invention provides thiourea-Pd(0) complexes that are air and moisture stable, highly active catalysts for the Heck reactions of aryl halides. More particularly, the invention provides the N,N'-disubstituted monothiourea ligand represented by generic structure I:

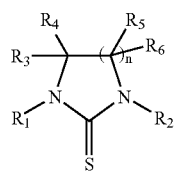

I wherein n is an integer in the range of 1 to 8 inclusive; $R_1$ and $R_2$ are selected, independently for each occurrence, from the groups consisting of alkyl, cycloalkyl, aryl, aralkyl, and $—(CH_2)_m—R_{80}$; $R_3$, $R_4$, $R_5$, and $R_6$ are selected, independently for each occurrence, from the groups consisting of H, alkyl, halogenated alkyl, cycloalkyl, aryl, aralkyl, $—(CH_2)_m—R_{80}$, $COOR_v$ (where $R_v$=alkyl, cycloalkyl, aryl, aralkyl, and $—(CH_2)_m—R_{80}$), and $CONR_uR_v$ (where $R_u$ or $R_v$=H, alkyl, cycloalkyl, aryl, aralkyl, and $—(CH_2)_m—R_{80}$); $R_{80}$ represents unsubstituted or substituted aryl, cycloalkyl, cycloalkenyl, or polycycle; m is independently for each occurrence an integer in the range of 0 to 8 inclusive; and the ligand, when chiral, is a mixture of enantiomers or a single enantiomer.

The bis-thiourea ligand represented by generic structure II:

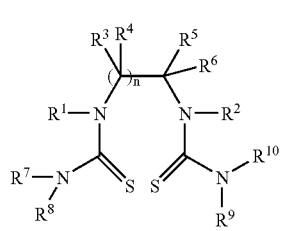

II wherein n is an integer in the range of 1 to 8 inclusive; $R_1$ and $R_2$ are selected, independently for each occurrence, from the groups consisting of alkyl, cycloalkyl, aryl, aralkyl, and $—(CH_2)_m—R_{80}$; $R_3$, $R_4$, $R_5$, $R_6$, $R_7$, $R_8$, $R_9$, and $R_{10}$ are selected, independently for each occurrence, from the groups consisting of H, alkyl, halogenated alkyl, cycloalkyl, aryl, aralkyl, $—(CH_2)_m—R_{80}$, $COOR_v$ (where $R_v$=alkyl, cycloalkyl, aryl, aralkyl, and $—(CH_2)_m—R_{80}$), and $CONR_uR_v$ (where $R_u$ or $R_v$=H, alkyl, cycloalkyl, aryl, aralkyl, and $—(CH_2)_m—R_{80}$); $R_{80}$ represents unsubstituted or substituted aryl, cycloalkyl, cycloalkenyl, or polycycle; m is independently for each occurrence an integer in the range of 0 to 8 inclusive; and the ligand, when chiral, is a mixture of enantiomers or a single enantiomer.

The bis-thiourea ligand represented by generic structure III:

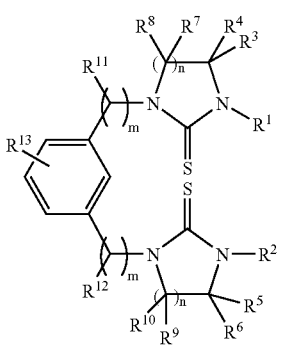

III wherein n is an integer in the range of 1 to 8 inclusive; $R_1$ and $R_2$ are selected, independently for each occurrence, from the groups consisting of alkyl, cycloalkyl, aryl, aralkyl, and $—(CH_2)_m—R_{80}$; $R_3$, $R_4$, $R_5$, $R_6$, $R_3$, $R_5$, $R_6$, $R_7$, $R_8$, $R_9$, $R_{10}$, $R_{11}$, $R_{12}$, $R_{13}$ are selected, independently for each occurrence, from the groups consisting of H, alkyl, halogenated alkyl, cycloalkyl, aryl, aralkyl, $—(CH_2)_m—R_{80}$, $COOR_v$ (where $R_v$=alkyl, cycloalkyl, aryl, aralkyl, and $—(CH_2)_m—R_{80}$), and $CONR_uR_v$ (where $R_u$ or $R_v$=H, alkyl, cycloalkyl, aryl, aralkyl, and —$(CH_2)_m$—$R_{80}$); $R_{80}$ represents unsubstituted or substituted aryl, cycloalkyl, cycloalkenyl, or polycycle; m is independently for each occurrence an integer in the range of 0 to 8 inclusive; and the ligand, when chiral, is a mixture of enantiomers or a single enantiomer.

DETAILED DESCRIPTION OF THE PREFERRED EMBODIMENTS

Figure 1:
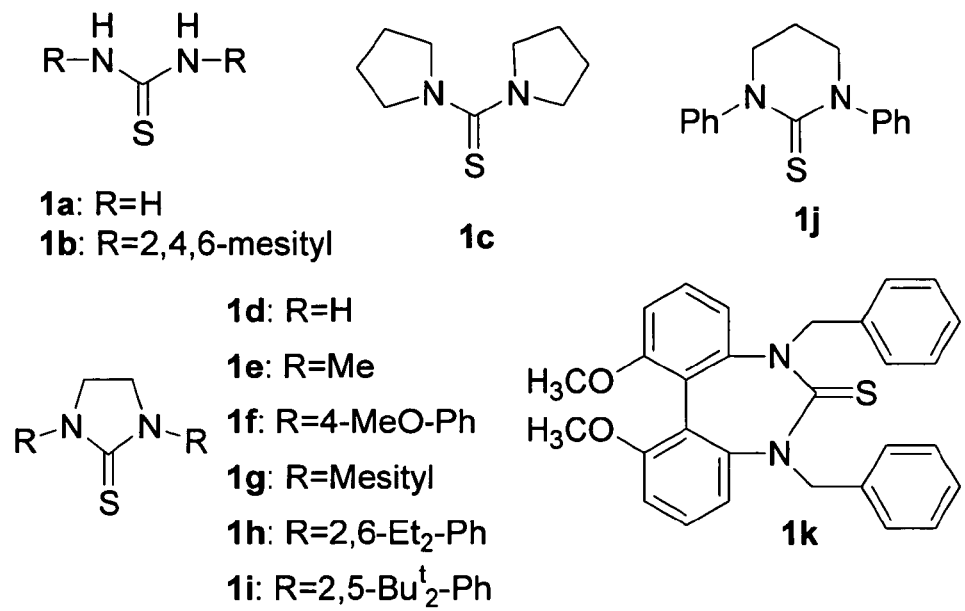
FIG. 1 shows some representative structures of thiourea ligands I.
Figure 2:
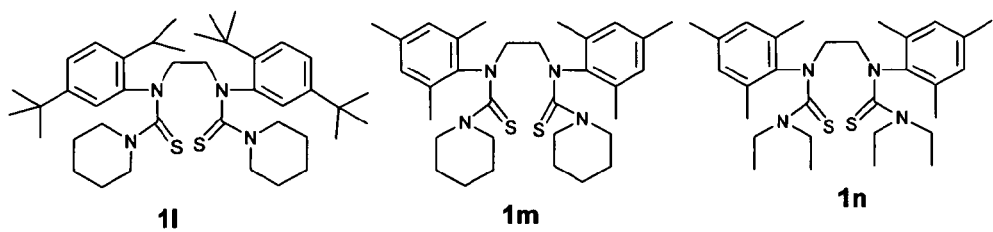
FIG. 2 shows some representative structures of thiourea ligands II.
Figure 3:
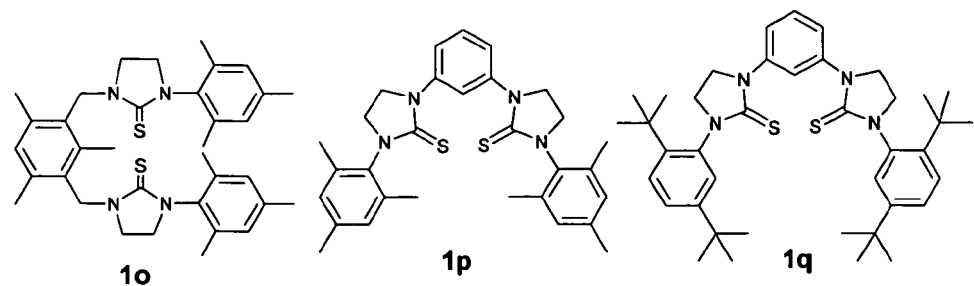
FIG. 3 shows some representative structures of thiourea ligands III.
Figure 4:
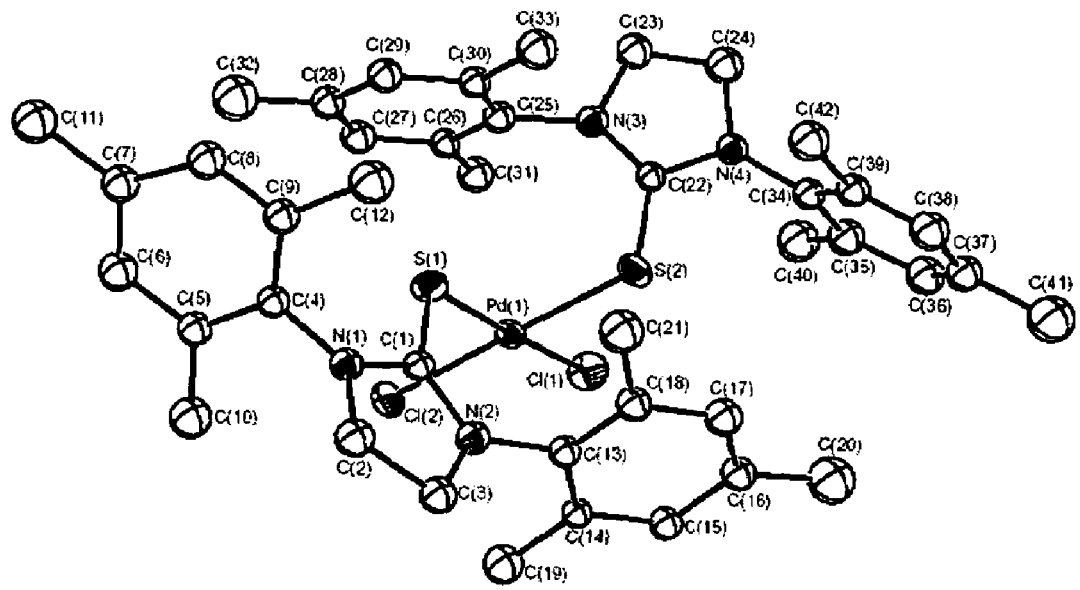
FIG. 4 shows structures of cis- and trans-$PdCl_2$·$(1g)_2$. (Hydrogen atoms have been omitted for clarity. Thermal ellipsoids are shown at 30% probability).
Figure 4:
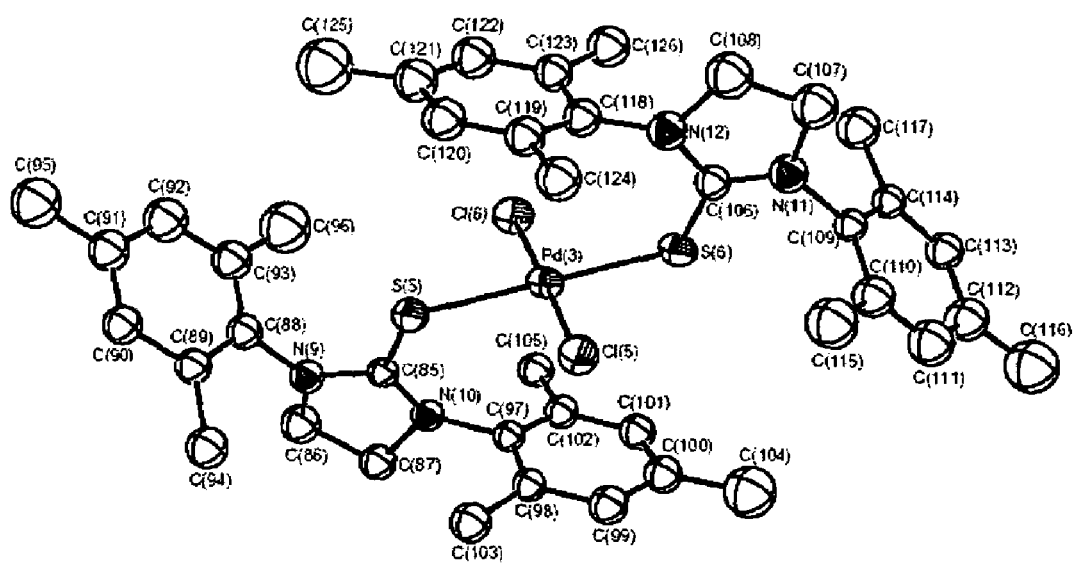

The invention provides acyclic and cyclic thioureas 1a-q (FIGS. 1-3) and complexes thereof with Pd(0) or Pd(II) (FIG. 4), which serve as catalysts for the Heck reaction between iodobenzene and methyl acrylate at 100° C. (Table 1).

TABLE 1

Screening thiourea ligands for the Pd-catalyzed Heck reaction of iodobenzene with methyl acrylate[a]

ArI + ＝＼$CO_2Me$ →[$Pd(dba)_2$/ligand / $NEt_3$, DMF / 100° C.] Ar＼＝／$CO_2Me$

| entry | ligand | Pd (mol %) | time (h) | yield[b] | TON |
|---|---|---|---|---|---|
| 1 | 1e | 0.1 | 1 | >99 | $10^3$ |
| 2 | 1g | 0.01 | 2 | >99 | $10^4$ |
| 3 | 1h | 0.01 | 2 | >99 | $10^4$ |
| 4 | 1i | 0.01 | 1.5 | >99 | $10^4$ |
| 5 | 1l | 0.01 | 6 | 86 | $8.6 \times 10^3$ |
| 6 | 1n | 0.01 | 4 | 95 | $9.5 \times 10^3$ |
| 7 | 1o | 0.01 | 4 | 45 | $4.5 \times 10^3$ |
| 8 | 1p | 0.01 | 4 | 99 | $10^4$ |
| 9 | 1q | 0.01 | 2 | 99 | $10^4$ |
| 10 | 1i | 0.0001 | 48 | 50 | $5 \times 10^5$ |
| 11[c] | 1n | 0.001 | 0.5 | 99 | $10^5$ |
| 12[d] | 1q | 0.0002 | 5 | 99 | $5 \times 10^5$ |
| 13[d] | 1n | 0.0001 | 12 | 99 | $10^6$ |

[a]Reactions were conducted under aerobic conditions.
[b]Yield was determined by $^1$H NMR spectroscopy using nitrobenzene as the internal standard.
[c]At 150° C.
[d]At 180° C. under solvent-free condition The reactions were conducted in air and that all the reagents were used directly as received. The structure of each thiourea ligand has a great influence on the catalytic efficacy of its palladium complex. Acyclic thioureas 1a-c were almost completely inactive, as was also the case for the cyclic thiourea 1d featuring an NH moiety. Good activity was observed, however, when using the N,N'-disubstituted bulky thioureas 1e-1q of different ring sizes as the ligands (Table 1 entries 1-8); the catalyst loading could be lowered down to 0.0001 mol %. The reaction also could be conducted at high temperature under solvent-free conditions without affecting the catalytic efficacy (entries 12 and 13).

The catalytic efficacy of the thiourea 1g-Pd(0) and 1q-Pd(0) complex in the Heck reaction was studied further with a number of aryl halides and olefins at 100-130° C. Table 2 indicates that high yields were obtained using 0.01 mol % Pd catalyst for olefins such as butyl acrylates (entries 1-2), Olefins that are α- or β-subsituted are also suitable substrates and give trisubstituted olefins,[12] but higher catalyst loadings and reaction temperatures were required (entries 3-4). In general, higher catalyst loadings and temperatures were required to force the completion of the reactions of the aryl bromides compared to the case of aryl iodides (entries 5-8). 3-Bromopyridine was also efficiently coupled with styrene in 90% yield in the presence of 0.1 mol % of Pd (entry 9). The deactivated bromide could be coupled at higher temperature (entry 10, 160° C.).

TABLE 2

Heck reaction of aryl iodides and bromides with olefins[a]

ArX + $R^1$＼／$R^2$／$R^3$ →[$Pd(dba)_2$/1g or 1q / base, solvent] $R^1$＼／$R^2$／Ar＼$R^3$

| entry | ligand | ArI | $R^1$＼／$R^2$／$R^3$ | Pd (mol %) | time (h) | yield (%)[b] |
|---|---|---|---|---|---|---|
| 1 | 1g | PhI | ＝＼$CO_2Bu^n$ | 0.01 | 2 | 99 |
| 2 | 1q | $H_3CO$—⟨⟩—I | ＝＼$CO_2Bu^n$ | 0.01 | 3 | 99 |

TABLE 2-continued

Heck reaction of aryl iodides and bromides with olefins[a]

ArX + R¹R³C=CR²  →(Pd(dba)₂/1g or 1q, base, solvent)→  ArR¹C=CR²R³

| entry | ligand | ArI | R¹R³C=CR² | Pd (mol %) | time (h) | yield (%)[b] |
|---|---|---|---|---|---|---|
| 3 | 1g | PhI | CH=CH-CO₂Me (trans) | 1 | 10 | 88 |
| 4 | 1q | 4-H₃CO-C₆H₄-I | CH₂=C(CH₃)-CO₂Me | 0.5 | 5 | 68 |
| 5 | 1g | 4-H₃COC-C₆H₄-Br | COOMe | 0.1 | 15 | 92 |
| 6 | 1g | 4-H₃COC-C₆H₄-Br | Ph | 0.1 | 15 | 99 |
| 7 | 1g | PhBr | Ph | 0.1 | 24 | 74 |
| 8 | 1q | 3-O₂N-C₆H₄-Br | CH₂=CH-COOBuⁿ | 0.1 | 10 | 99 |
| 9 | 1g | 3-Br-pyridine | Ph | 0.1 | 24 | 90 |
| 10 | 1q | 4-H₃CO-C₆H₄-Br | CH=CH-Ph | 0.5 | 24 | 76 |

Beller[13] reported that the Heck reactions of aryl chlorides could be greatly improved when using Bu$_4$NBr as an ionic liquid solvent.[14] In fact, this system is also suitable for the thiourea 1g-Pd(0)-catalyzed Heck reactions of deactivated bromides and activated chlorides, when the reaction temperature is elevated slightly. The results were summarized in Table 3. Excellent yields were achieved for deactivated bromides after their reaction for 24 h in the presence of 0.5 mol % of Pd (entries 1-3), but incomplete conversion occurred when using 0.2 mol % Pd catalyst (entry 4). Under the same conditions, activated aryl chlorides were coupled successfully with styrene within 24 h when using 1 mol % of the Pd catalyst (entries 5-7). n-Butyl acrylate displayed reactivity that was slightly lower than that of styrene, but good yields were also obtained (entries 8-10). Chorobenzene itself, however, was completely inert, even when we used a higher loading of the Pd catalyst (2 mol %) (entry 11).

TABLE 3

Heck reactions of deactivated bromides and activated chlorides with olefins $$\text{ArX} + \overset{R}{=\!=\!=} \xrightarrow[\text{NaOAc, TBAB}]{\text{Pd(dba)}_2/1g} \underset{\text{Ar}}{\overset{R}{=\!=\!=}}$$
135° C.

| entry | ArX | R | Pd (mol %) | time (h) | yield (%)$^b$ |
|---|---|---|---|---|---|
| 1 | H$_3$CO—C$_6$H$_4$—Br | Ph | 0.5 | 24 | 99 |
| 2 | H$_3$CO—C$_6$H$_4$—Br | COO$^n$Bu | 0.5 | 24 | 99 |
| 3 | (CH$_3$)$_2$N—C$_6$H$_4$—Br | COO$^n$Bu | 0.5 | 24 | 97 |
| 4 | H$_3$CO—C$_6$H$_4$—Br | Ph | 0.2 | 30 | 80 |
| 5 | H$_3$COC—C$_6$H$_4$—Cl | Ph | 1 | 24 | 96 |
| 6 | H$_3$COC—C$_6$H$_4$—Cl | Ph | 0.5 | 30 | 67 |
| 7 | 2-NO$_2$-C$_6$H$_4$—Cl | Ph | 1 | 24 | 99 |
| 8 | H$_3$COC—C$_6$H$_4$—Cl | COO$^n$Bu | 2 | 24 | 77 |
| 9 | PhOC—C$_6$H$_4$—Cl | COO$^n$Bu | 1 | 24 | 80 |
| 10 | 2-NO$_2$-C$_6$H$_4$—Cl | COO$^n$Bu | 1 | 24 | 90 |

TABLE 3-continued

Heck reactions of deactivated bromides and activated chlorides with olefins

| entry | ArX | R | Pd (mol %) | time (h) | yield (%)[b] |
|---|---|---|---|---|---|
| 11 | ![Cl-phenyl] | Ph | 2 | 24 | <5 |

The Pd-catalysed Suzuki cross-coupling reaction of aryl halides with aryl boric acids provides a general and efficient synthetic route to biaryl compounds and has found wide application in many areas of organic synthesis.[15] The operationally simple and air-stable catalytic system of thiourea-Pd catalyst inspired us to investigate its scope in Suzuki reaction. As revealed in Table 4 using 1q as the ligand, for p-iodoanisole, excellent isolated yield was obtained at a loading of 0.01 mol % Pd at 100° C. after 3h under aerobic conditions (Table 3, entry 1).

Encouraged by the result, we began to evaluate the coupling reaction of aryl bromides with aryl boric acids. For activated bromides, almost quantitative yields were achieved within 3h in the presence of 0.1 mol % Pd under the same conditions (entries 2-6). On the other hand, low yield was obtained when deactivated p-bromoanisole was applied at 0.5 mol % Pd at 120° C. (entry 7), and similar results were gained when a bulky monodentate 1i was used (entry 8). However, the yield could be increased adding 20 mol % TBAB (entry 9). For 3,5-difluorophenylboric acid, better result could be obtained when the reaction was conducted in neat TBAB (entry 10). Acceptable yield was achieved for p-nitrochlorobenzene at 1 mol % Pd adding 20 mol % TBAB (entry 11 vs 12). Notably 1-bromostyrene also displayed high reactivity to phenylboric acid in thiourea-Pd system (entry 13). Moreover, potassium aryl trifluoroborates[16] have been found to be more reactive than the corresponding organoboric acid, and high yields were obtained at only 0.1 mol % Pd at 100° C. (entries 14 and 15). We also conducted the Suzuki reaction at further decreased catalyst loading (0.01 mol %), and quantitative yield was obtained for 3-nitro-bromobenzene at 120° C. in 3h (entry 16).

TABLE 4

Suzuki coupling reaction catalyzed by 1q-Pd(dba)₂

$$ArX + Ar^1B(OH)_2 \xrightarrow[K_2CO_3, NMP, H_2O]{Pd(bda)_2\text{-}1q} Ar\text{---}Ar^1$$

| Entry | Ar¹X | Ar²B(OH)₂ | Pd (mol %) | T (° C.) | t (h) | Yield (%) |
|---|---|---|---|---|---|---|
| 1 | H₃CO—⬡—I | PhB(OH)₂ | 0.01 | 100 | 3 | 92 |
| 2 | OHC—⬡—Br | PhB(OH)₂ | 0.1 | 100 | 3 | 92[c] |
| 3 | MeOOC—⬡—Br | PhB(OH)₂ | 0.1 | 100 | 3 | 90 |
| 4 | O₂N—⬡—Br | PhB(OH)₂ | 0.1 | 100 | 3 | 99 |
| 5 | O₂N—⬡—Br | F₃C—⬡(F₃C)—B(OH)₂ | 0.1 | 100 | 2 | 97 |

TABLE 4-continued
Suzuki coupling reaction catalyzed by 1q-Pd(dba)$_2$
| Entry | Ar$^1$X | Ar$^2$B(OH)$_2$ | Pd (mol %) | T (° C.) | t (h) | Yield (%) |
|---|---|---|---|---|---|---|
| 6 | 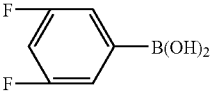 | 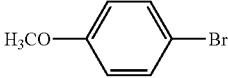 | 0.1 | 100 | 2 | 99 |
| 7 | 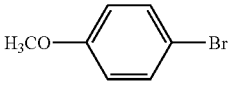 | PhB(OH)$_2$ | 0.5 | 120 | 10 | 33 |
| 8[c] | 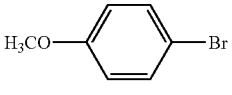 | PhB(OH)$_2$ | 0.5 | 120 | 10 | 27 |
| 9[d] | 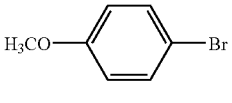 | PhB(OH)$_2$ | 0.5 | 120 | 12 | 67 |
| 10[e] | 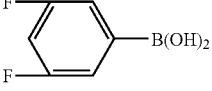 | 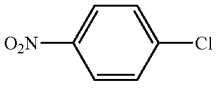 | 0.5 | 130 | 12 | 51 |
| 11[f] | 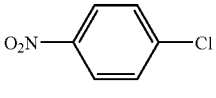 | PhB(OH)$_2$ | 1 | 130 | 40 | 10 |
| 12[d,f] |  | PhB(OH)$_2$ | 1 | 130 | 24 | 49 |
| 13 | 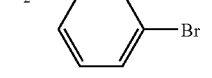 | PhB(OH)$_2$ | 0.1 | 100 | 1 | 80 |
| 14 | 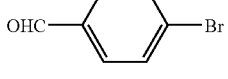 | PhBF$_3$K | 0.1 | 100 | 1 | 99 |
| 15 | 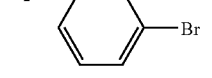 | PhBF$_3$K | 0.1 | 100 | 1.5 | 87 |
| 16 |  | PhB(OH)$_2$ | 0.01 | 120 | 3 | 99 |

EXAMPLE 1

Synthesis of Cyclic Thioureas 1f-1k

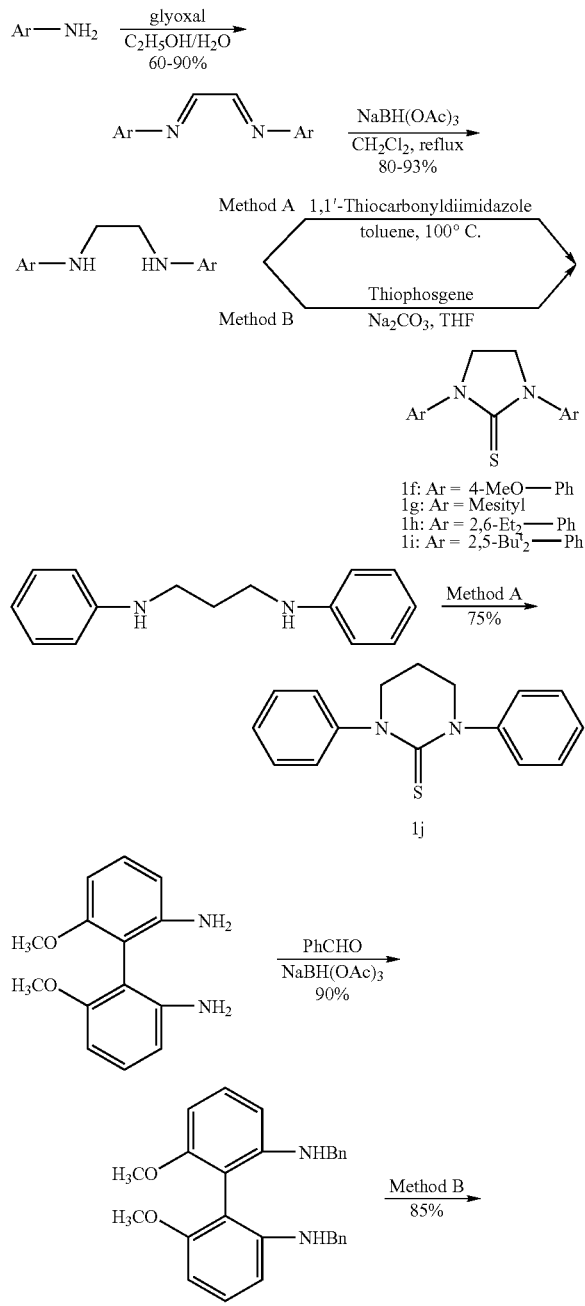

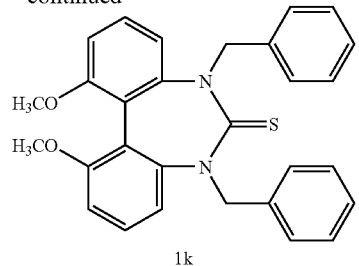

Two methods were used for the synthesis of cyclic thiourea ligands (Scheme 1)

Method A:

To a N,N'-diaryl diamine solution in dry toluene was added 1,1'-thiocarbonyl diimidazole (1.2 equiv). Then the solution was stirred at 100° C. and the reaction was monitored by TLC. After completion, the solution was diluted with ethyl acetate and washed with dilute HCl and brine. The organic layer was concentrated under vacuum. The pure thiourea was obtained through flash chromatography or recrystallization from 95% ethanol.

Method B:

To a stirred mixture of N,N'-diaryl diamine and $Na_2CO_3$ (1.5 equiv) in dry THF was added a solution of thiophosgene (1.2 equiv) in THF dropwise at room temperature. After stirring at room temperature overnight, water and ethyl acetate were added. The organic layer was washed with dilute HCl and brine, dried and concentrated. The pure thiourea was obtained through flash chromatography or recrystallization from 95% ethanol.

Preparation of 1f:

Using method A; 75% yield. M.p. 167-168° C; $^1$H NMR (300 MHz, $CDCl_3$) δ 7.42 (d, J=9.0 Hz, 4H), 6.95 (d, J=9.0 Hz, 4H), 4.08 (s, 4H), 3.81 (s, 6H); $^{13}$C NMR (75 MHz, $CDCl_3$) δ 182.2, 158.1, 138.8, 127.5, 114.2, 55.4, 49.8; IR ($cm^{-1}$): 1511, 1443, 1285; LRMS (EI): 314 ($M^+$, 100); HRMS (EI): calcd for $C_{17}H_{18}N_2O_2S$ ($M^+$) 314.1089, found 314.1088.

Preparation of 1g:

Using method B; 85% yield. M.p. 218-218.5° C.; $^1$H NMR (400 MHz, $CDCl_3$) δ 6.91 (s, 4H), 3.94 (s, 4H), 2.26 (s, 6H), 2.24 (s, 12H); $^{13}$C NMR (75 MHz, $CDCl_3$) δ 181.1, 138.2, 136.6, 134.5, 129.5, 47.6, 21.1, 17.8; IR ($cm^{-1}$): 1488, 1331, 1271; LRMS (FAB): 339 ($M^++1$, 100); HRMS (FAB): calcd for $C_{21}H_{26}N_2S$ ($M^++1$) 339.1894, found 339.1879.

Preparation of 1h:

Using method B; 70% yield. M.p. 152-153° C.; $^1$H NMR (300 MHz, $CDCl_3$) δ 7.32 (t, J=6.6 Hz, 2H), 7.20 (d, J=7.5 Hz, 4H), 4.02 (s, 4H), 2.80-2.70 (m, 4H), 2.69-2.60 (m, 4H), 1.33 (t, J=7.5 Hz, 12H); $^{13}$C NMR (75 MHz, $CDCl_3$) δ 182.6, 142.5, 136.1, 128.8, 126.5, 49.1, 24.0, 14.4; IR ($cm^{-1}$): 1484, 1285; LRMS (EI): 366 ($M^+$, 39), 337 (100); HRMS (EI): calcd for $C_{23}H_{30}N_2S$ ($M^+$) 366.2130, found 366.2120.

Preparation of 1i:

Diimine: 92% yield. $^1$H NMR (300 MHz, $CDCl_3$) δ 8.27 (s, 2H), 7.35 (d, J=8.3 Hz, 2H), 7.25 (d, J=8.3 Hz, 2H), 6.86 (s, 2H), 1.43 (s, 18H), 1.34 (s, 18H); $^{13}$C NMR (75 MHz, $CDCl_3$) δ 158.6, 150.1, 150.0, 140.4, 126.0, 123.8, 116.0, 35.3, 34.4, 31.3, 30.5; IR (cm⁻¹): 1609, 1492, 1265; LRMS (EI): 432 (M⁺, 100); HRMS (EI): calcd for $C_{30}H_{44}N_2$ (M⁺) 432.3504, found 432.3504.

Diamine: 90% yield. ¹H NMR (300 MHz, CDCl₃) δ 7.18 (d, J=6.1 Hz, 2H), 6.80 (s, 2H), 6.75 (d, J=6.1 Hz, 2H), 4.18 (br s, 2H, NH), 3.57 (s, 4H), 1.39 (s, 18H), 1.32 (s, 18H); ¹³C NMR (75 MHz, CDCl₃) δ 149.9, 146.2, 131.2, 126.0, 114.6, 110.0, 45.0, 34.4, 33.8, 31.4, 30.2; IR (cm⁻¹): 3688, 3601, 1561, 1265; LRMS (EI): 436 (M⁺, 20), 219 (100); HRMS (EI): calcd for $C_{30}H_{48}N_2$(M⁺) 436.3817, found 436.3817.

Thiourea Ii was prepared using method B. A solution of Thiophosgene in dilute THF must be dropped very slowly. 1i was isolated as a white solid (75% yield) after flash chromatography on silica gel. M.p. 212-214° C.; ¹H NMR (400 MHz, CDCl₃) δ 7.45 (d, J=8.5 Hz, 2H), 7.32 (d, J=8.5 Hz, 2H), 7.02 (s, 2H), 4.06-4.03 (m, 2H), 3.93-3.91 (m, 2H), 1.50 (s, 18H), 1.30 (s, 18H); ¹³C NMR (100 MHz, CDCl₃) δ 183.5, 150.4, 145.0, 140.8, 128.0, 127.8, 125.3, 53.4, 35.4, 34.3, 32.1, 31.3; IR (cm⁻¹): 1418, 1275; LRMS (FAB): 479 (M⁺+H); FAB-HRMS: calcd for $C_{31}H_{46}N_2S$ (M⁺+H) 479.3460, found 479.3460.

Preparation of 1j:

Using method A, 75% yield. M.p. 173-174° C.; ¹H NMR (300 MHz, CDCl₃) δ 7.41-7.15 (m, 10H), 3.82-3.77 (m, 4H), 2.32-2.24 (m, 2H); ¹³C NMR (75 MHz, CDCl₃) δ 180.7, 147.4, 129.2, 127.4, 125.8, 51.4, 22.3; IR (cm⁻¹): 1494, 1285; LRMS (EI): 268 (M⁺, 73); EI-HRMS: calcd for $C_{16}H_{16}N_2S$ (M⁺) 268.1034, found 268.1015.

Preparation of 1k:

To a stirred suspension of racemic 2,2'-diamino-6,6'-dimethoxybiphenyl[2] (60 mg, 0.25 mmol) and NaBH(OAc)₃ (212 mg, 1 mmol) in dichloromethane (10 mL) was added a solution of benzaldehyde (0.06 ml, 0.58 mmol) in dichloromethane (2 mL) dropwise at room temperature. Then the mixture was stirred overnight. Flash chromatography on silica gel gave N,N'-dibenzyl diamine as a white solid (94 mg, 90%). ¹H NMR (300 MHz, CDCl₃) δ 7.26-7.11 (m, 12H), 6.38 (d, J=8.2 Hz, 2H), 6.32 (d, J=7.7 Hz, 2H), 4.32 (s, 4H), 4.17 (br s 2H), 3.70 (s, 6H); ¹³C NMR (75 MHz, CDCl₃) δ 158.1, 147.3, 139.9, 129.6, 128.4, 126.7, 126.6, 107.2, 104.2, 100.6, 55.7, 47.5; IR (cm⁻¹): 3432, 3086, 3051, 2938, 1586, 496, 1472, 1422, 1282, 1131; LRMS (EI): 424 (M⁺, 33), 333 (100); HRMS (EI): calcd for $C_{28}H_{28}N_2O_2S$ (M⁺) 424.2151, found 424.2138.

Thiourea 1k was prepared using method B, 85% yield. M.p. 179-180° C.; ¹H NMR (400 MHz, CDCl₃) δ 7.27 (t, J=8.2 Hz, 2H), 7.04-7.00 (m, 6H), 6.88 (d, J=8.2 Hz, 2H), 6.83-6.80 (m, 6H), 5.72 (d, J=15.3 Hz, 2H), 4.81 (d, J=15.3 Hz, 2H), 3.75 (s, 6H); ¹³C NMR (75 MHz, CDCl₃) δ 199.6, 157.2, 147.7, 137.1, 128.7, 127.9, 127.5, 126.7, 121.8, 113.9, 108.8, 56.8, 55.9; IR (cm⁻¹): 3051, 1592, 1579, 1464, 1420, 1245, 1190; LRMS (EI): 466 (M⁺, 100), 375 (86); HRMS (EI): calcd for $C_{29}H_{26}N_2O_2S$ (M⁺) 466.1715, found 466.1718.

EXAMPLE 2

Synthesis of Acyclic Bis-Thiourea Ligands

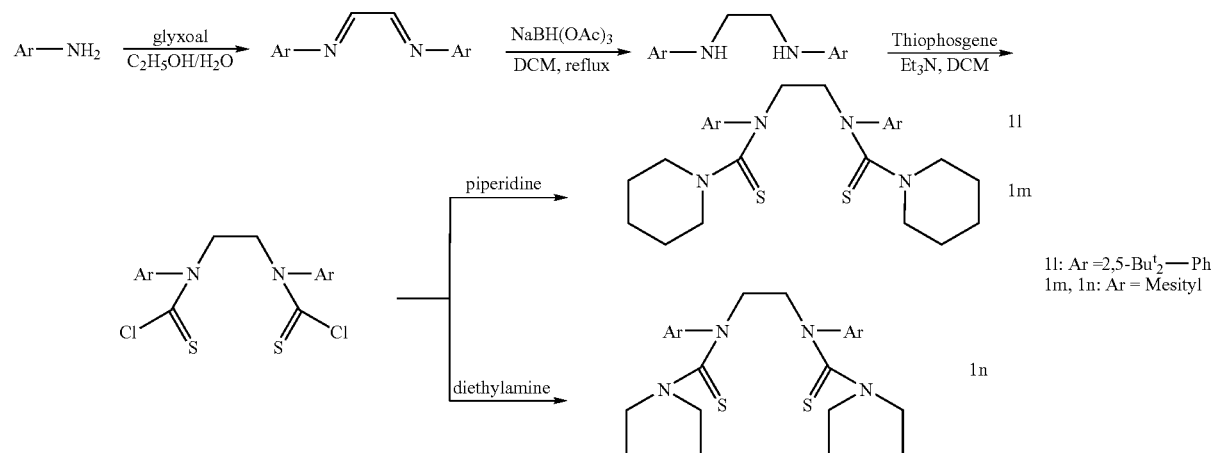

Scheme 2

1l: Ar =2,5-Bu$^t_2$—Ph
1m, 1n: Ar = Mesityl

A solution of N,N'-diaryl diamine (1.0 mmol) and NEt₃ (3 equiv) in THF was dropped to a stirred solution of thiophosgene (3.0 equiv) in dry THF at 0° C. After stirred at room temperature overnight, the organic layer was washed with water, dried and concentrated.

For the synthesis of acyclic bis-thiourea, the dichloride obtained above and excess secondary amine were heated at 100° C. in a sealed pressure tube for 24 hours. Then the solution was diluted with EtOAc and washed with dilute HCl and brine. The organic layer was dried and concentrated. Flash chromatography gave the pure bis-thiourea as a white solid.

1l: White solid, 95% yield; m.p 225-226° C.; ¹H NMR (400 MHz, CDCl₃) δ 7.37-7.34 (m, 2H), 7.21-7.18 (m, 2H), 7.18-7.00 (m, 2H), 4.87-4.79 (m, 2H), 4.15-4.11 (m, 2H), 3.54-3.35 (m, 8H), 1.44-1.19 (m, 48H); ¹³C NMR (100 MHz, CDCl₃) δ 190.0, 149.1, 142.9, 141.3, 129.8, 127.4, 124.1, 54.0, 52.5, 35.6, 34.0, 32.0, 31.1, 25.2, 24.2; IR (cm⁻¹): 2958, 2865, 1609, 1440, 1397, 1362, 1244, 1185, 1133, 1026; ESI LRMS: 690(M, 2), 359(100); EI HRMS: calcd for $C_{42}H_{66}N_4S_2$ 690.4729, found 690.4717.

1m: White solid, 40% yield for two steps; m.p 222-224° C.; ¹H NMR (400 MHz, CDCl₃) δ 6.83 (s, 4H), 4.29 (s, 4H), 3.30-3.27 (m, 8H), 2.25 (s, 6H), 2.18 (s, 12H), 1.39-1.36 (m, 4H), 1.17-1.15 (m, 8H); ¹³C NMR (100 MHz, CDCl₃) δ 188.3, 141.3, 136.1, 134.3, 130.0, 51.9, 50.9, 25.2, 24.2, 20.7, 19.1; IR (cm$^{-1}$): 2934, 2851, 1609, 1473, 1422, 1369, 1245, 1185, 1159, 1131, 1027; EI LRMS: 550 (M, 34), 152 (100); EI HRMS: calcd for $C_{32}H_{46}N_4S_2$ 550.3164, found 550.3158.

1n: White solid, 38% yield for two steps; m.p 197-199° C.; $^1$H NMR (400 MHz, CDCl$_3$) δ 6.82 (s, 4H), 4.29 (s, 4H), 3.30 (q, J=6.8 Hz, 8H), 2.24 (s, 6H), 2.21 (s, 12H), 0.73 (t, J=6.8 Hz, 12H); $^{13}$C NMR (100 MHz, CDCl$_3$) δ 189.9, 141.6, 136.4, 135.0, 51.3, 46.0, 20.8, 19.2, 11.7; IR (cm$^{-1}$): 2963, 2929, 1651, 1486, 1441, 1411, 1370, 1348, 1274, 1223, 1185, 1152, 1120, 1081, 1013; EI LRMS: 526 (M, 42), 277 (100); EI HRMS: calcd for $C_{30}H_{46}N_4S_2$ 526.3164, found 526.3168.

EXAMPLE 3

Synthesis of Cyclic Bis-Thiourea Ligand 1o

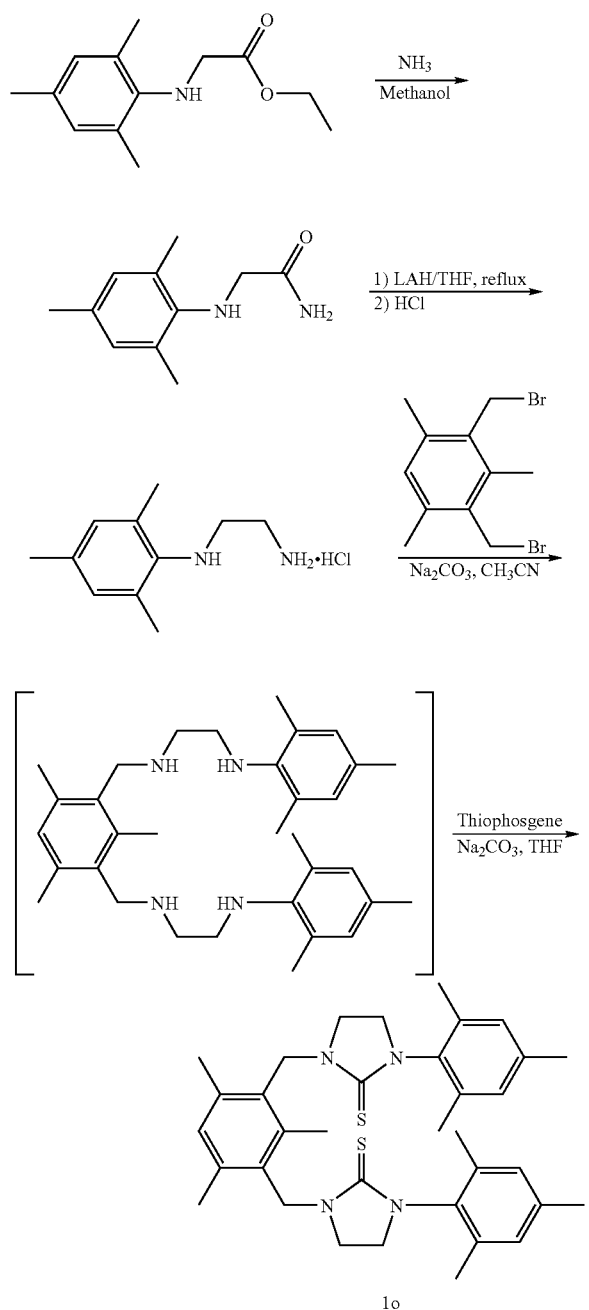

Preparation of 1o:

To a stirred mixture of diamine salt (2.0g, 9.2 mmol) and Na$_2$CO$_3$ (0.85g, 8 mmol) in CH$_3$CN (15 ml) was added slowly a solution of Bis(bromomethy) mesitylene (0.72g, 2.3 mmol) in CH$_3$CN (10 ml) at 81° C. The resulting mixture was refluxed for 24h. Then the mixture was diluted with ethyl acetate and washed with brine, dried and concentrated. The resulting oil was dissolved in THF (30 ml) and Na$_2$CO$_3$ (1.27g, 12 mmol) was added. Thiophosgene (0.7 ml, 9 mmol) in THF (10 ml) was dropped very slowly at room temperature. After stirred overnight, THF was removed, and water (20 ml) and ethyl acetate (40 ml) were added. The organic layer was washed with dilute HCl and brine, dried and concentrated. The pure bis-thiourea 1o was obtained through flash chromatography (20% ethyl acetate/petroleum ether) as a white solid (150 mg, 11%).

1o: m.p>230° C.; $^1$H NMR (400 MHz, CDCl$_3$) δ 6.97 (s, 1H), 6.95 (s, 4H), 4.97 (s, 4H), 3.66 (t, J=8.4 Hz, 4H), 3.41 (t, J=8.4 Hz, 4H), 2.43 (s, 3H), 2.40 (s, 6H), 2.29 (s, 6H), 2.22 (s, 12H); $^{13}$C NMR (100 MHz, CDCl$_3$) δ 181.7, 138.6, 138.1, 137.8, 136.5, 134.7, 130.8, 130.7, 129.4, 46.9, 46.3, 45.5, 21.0, 20.4, 17.7, 16.2; IR (cm$^{-1}$): 2917, 1609, 1489, 1437, 1408, 1326, 1309, 1273, 1233, 1033; ESI LRMS: 585 (M+1, 100); ESI HRMS: calcd for $C_{35}H_{44}N_4S_2$+Na 607.2905, found 607.2883.

EXAMPLE 4

Synthesis of Cyclic Bis-Thiourea Ligands 1p and 1q

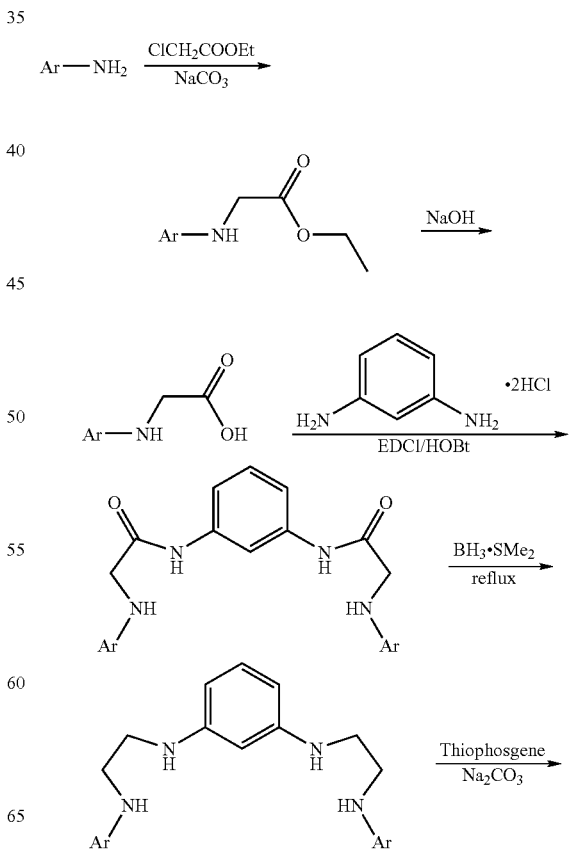

-continued

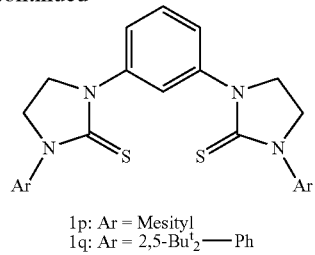

1p: Ar = Mesityl
1q: Ar = 2,5-Bu$^t_2$—Ph

Preparation of 1p and 1q:

Borane-dimethylsulfide (2M in THF) (3.6 ml 7.2 mmol, 8equiv.) was added to a solution of diamide (0.9 mmol) in THF (20 ml) at 0° C. Then the solution was refluxed overnight. After cooling to room temperature, methanol was added very slowly to destroy the excess borane. The solvent was removed. Methanol (10 ml) was added and removed again under reduced pressure. The resulting tetraamine was directly used in the next step.

To a stirred mixture of tetraamine obtained above and Na$_2$CO$_3$ (6 equiv.) in dry THF was added a dilute solution of thiophosgene in THF. Then the mixture was stirred at room temperature overnight. The pure cyclic bis-thiourea was obtained as a white solid through flash chromatography and recrystalyzation from ethanol.

1p: White solid, 45% yield for two steps; m.p>230° C.; $^1$H NMR (400 MHz, CDCl$_3$) δ 8.20 (s, 1H), 7.51-7.44 (m, 3H), 6.97 (s, 4H), 4.29 (t, J=8.4 Hz, 4H), 3.91 (t, J=8.4 Hz, 4H), 2.31 (s, 6H), 2.28 (s, 12H); $^{13}$C NMR (100 MHz, CDCl$_3$) δ 180.7, 141.0, 138.3, 136.3, 134.7, 129.4, 128.6, 121.1, 120.2, 49.3, 47.2, 21.0, 17.8; IR (cm$^{-1}$): 2917, 1604, 1489, 1421, 1306, 1277, 1076; ESI LRMS: 515 (M+1, 100); ESI HRMS: calcd for C$_{30}$H$_{34}$N$_4$O$_4$S$_2$+H 515.2303, found 515.2294.

1q: White solid, 41% yield for two steps; m.p>2300C; $^1$HNMR (400 MHz, CDCl$_3$) δ 8.24-8.22 (m, 1H), 7.53-7.43 (m, 3H), 7.38 (d, J=2.0 Hz, 2H), 7.35 (d, J=2.0 Hz, 2H), 7.11 (s, 2H), 4.29-4.18 (m, 4H), 4.13-4.07 (m, 2H), 4.01-3.93 (m, 2H), 1.48 (s, 18H), 1.34 (s, 18H); $^{13}$C NMR (100 MHz, CDCl$_3$) δ 184.1, 150.5, 145.0, 141.2, 139.6, 128.8, 128.7, 128.2, 127.5, 125.5, 121.8, 121.6, 121.2, 52.6, 49.4, 35.4, 34.3, 31.9, 31.2; IR (cm$^{-1}$): 2960, 1604, 1559, 1475, 1414, 1297, 1084; ESI LRMS: 655 (M+1, 37), 639 (100); ESI HRMS: calcd for C$_{40}$H$_{54}$N$_4$S$_2$+H 655.3868, found 655.3864

EXAMPLE 5

General Procedure for Heck Reaction of Aryl Iodides and Olefins

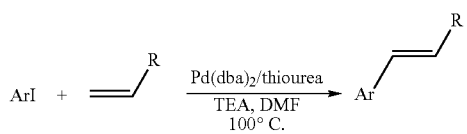

Pd(dba)$_2$ (1.5 mg, 0.0025 mmol) and thiourea (4 equiv) were stirred in DMF (0.5 mL) for 0.5 h at rt. Iodobenzene (0.28 mL, 2.5 mmol, substrate/catalyst ratio=1000:1) and methyl acrylate (0.27 mL, 3.0 mmol) and TEA (0.42 mL, 3.0 mmol) were then added. The flask was sealed with rubber septa and heated at 100° C. (the same result was obtained when the reaction was conducted with a condenser in open air). After the indicated time, the solution was diluted with ethyl acetate (20 mL) and washed with water and brine. Ethyl acetate was removed under vacuum and nitrobenzene (0.128 mL) was added as an internal standard. The yield of coupling product was determined by $^1$H NMR (400 MHz or 300 MHz) analysis, by comparing the peak intensities of the α/β-H of the product and the ortho-H of nitrobenzene (internal standard).

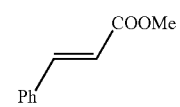

$^1$H NMR (300 MHz, CDCl$_3$) δ 7.67-7.63 (m, 2H), 7.54 (d, J=4.1 Hz, 2H), 7.38 (d, J=3.3 Hz, 1H), 7.10 (t, J=6.5 Hz, 1H), 6.44 (d, J=16.1 Hz, 1H), 3.81 (s, 3H). To determine the reaction yield, the product peak at 6.44 ppm was selected for comparison with that of the ortho-H (at 8.20 ppm) of nitrobenzene (internal standard).

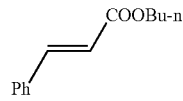

$^1$H NMR (400 MHz, CDCl$_3$) δ 7.73 (d, J=16.0 Hz, 1H), 7.52-7.57 (m, 2H), 7.40-7.45 (m, 3H), 6.49 (d, J=16.0 Hz, 1H), 4.26 (t, J=6.9 Hz, 2H), 1.71-1.78 (m, 2H), 1.54-1.45 (m, 2H), 1.00 (t, J=7.4 Hz, 3H).

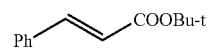

$^1$H NMR (300 MHz, CDCl$_3$) δ 7.73 (d, J=16.0 Hz, 1H), 7.53-7.57 (m, 2H), 7.40-7.45 (m, 3H), 6.49 (d, J=16.0 Hz, 1H), 1.34 (s, 9H).

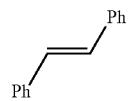

$^1$H NMR (300 MHz, CDCl$_3$) δ 7.53 (d, J=7.2 Hz, 4H), 7.38 (dd, J=7.1, 1.5 Hz, 4H), 7.28 (d, J=7.2 Hz, 2H), 7.13 (s, 2H).

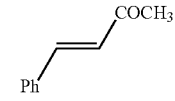

¹H NMR (300 MHz, CDCl₃) δ 7.55 (d, J=9.4 Hz, 2H), 7.52 (d, J=16.0 Hz, 1H), 7.40 (t, J=3.5 Hz, 3H), 6.72 (d, J=16.0 Hz, 1H), 2.39 (s, 3H).

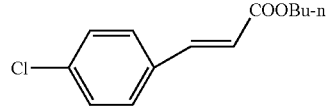

¹H NMR (300 MHz, CDCl₃) δ 7.63 (d, J=16.2 Hz, 1H), 7.43 (d, J=6.2 Hz, 2H), 7.35 (d, J=6.2 Hz, 2H), 6.40 (d, J=16.2 Hz, 1H), 4.26 (t, J=6.9 Hz, 2H), 1.78–1.71 (m, 2H), 1.54–1.45 (m, 2H), 1.00 (t, J=7.4 Hz, 3H).

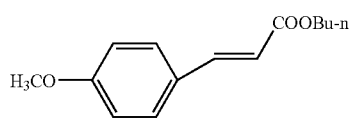

¹H NMR (400 MHz, CDCl₃) δ 7.68 (d, J=16.0 Hz, 1H), 7.51 (d, J=8.9 Hz, 2H), 6.94 (d, J=8.9 Hz, 2H), 6.36 (d, J=16.0 Hz, 1H), 4.25 (t, J=6.8 Hz, 2H), 3.87 (s, 3H), 1.76–1.70 (m, 2H), 1.52–1.46 (m, 2H), 1.02 (t, J=7.5 Hz, 3H).

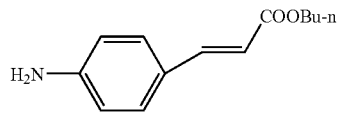

¹H NMR (400 MHz, CDCl₃) δ 7.70 (d, J=8.4 Hz, 2H), 7.56 (d, J=15.7 Hz, 1H), 6.62 (d, J=8.4 Hz, 2H), 6.51 (d, J=15.7 Hz, 1H), 6.17 (s, 2H), 4.26 (t, J=6.9 Hz, 2H), 1.78–1.77 (m, 2H), 1.54–1.45 (m, 2H), 1.00 (t, J=7.4 Hz, 3H).

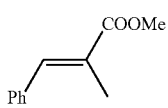

¹H NMR (300 MHz, CDCl₃) δ 7.55 (d, J=6.9 Hz, 2H), 7.40–7.19 (m, 4H), 3.82 (s, 3H), 2.13 (s, 3H).

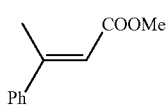

¹H NMR (300 MHz, CDCl₃) δ 7.53–7.45 (m, 3H), 7.37–7.35 (m, 2H), 6.13 (q, J=1.2 Hz, 1H), 3.75 (s, 3H), 2.58 (d, J=1.3 Hz, 3H).

EXAMPLE 6

General Procedure for Heck Reaction of Aryl Bromides and Olefins

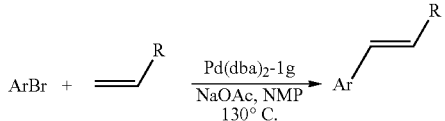

Pd(dba)₂ (1.5 mg, 0.0025 mmol) and thiourea 1g (3.4 mg, 0.01 mmol) were stirred in NMP (0.5 mL) for 0.5 h at rt. Aryl bromide (2.5 mmol, S/C=1000), olefin (3.8 mmol) and sodium acetate 330 mg (3.8 mmol) were added in turn. Then the flask was sealed with a septa and heated at 130° C. After indicated time, the solution was dilute with ethyl acetate (20 mL) and washed with water and brine. Ethyl acetate was removed under vacuum and nitrobenzene (0.128 mL) was added as internal standard. The yield of coupling product was determined by ¹H NMR (400 MHz or 300 MHz) analysis, by comparing the peak intensities of the cc/P—H of the product and the ortho-H of nitrobenzene (internal standard).

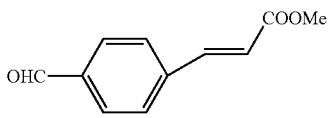

¹H NMR (300 MHz, CDCl₃) δ 9.99 (s, 1H), 7.87 (d, J=8.1 Hz, 2H), 7.70–7.62 (m, 3H), 6.52 (d, J=15.9 Hz, 1H), 3.79 (s, 3H).

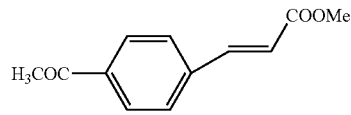

¹H NMR (300 MHz, CDCl₃) δ 7.80–7.75 (m, 3H), 7.42 (d, J=6.8 Hz, 2H), 6.34 (d, J=16.1 Hz, 1H), 3.63 (s, 3H), 2.42 (s, 3H).

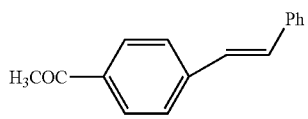

¹H NMR (400 MHz, CDCl₃) δ 7.53–7.45 (m, 4H), 7.36–7.32 (m, 4H), 7.28–7.26 (m, 2H), 7.17 (d, J=12.3 Hz, 1H), 7.07 (d, J=12.3 Hz, 1H), 2.55 (s, 3H).

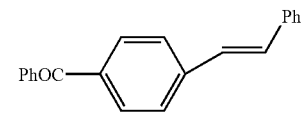

¹H NMR (300 MHz, CDCl₃) δ 7.85-7.32 (m, 15H), 6.24 (d, J=16.2 Hz, 1H).

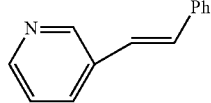

¹H NMR (300 MHz, CDCl₃) δ 8.70 (d, J=1.3 Hz, 1H), 8.45 (d, J=3.5 Hz, 1H), 7.52 (d, J=9.0 Hz, 1H), 7.36-7.33 (m, 2H), 7.30-7.25 (m, 4H), 7.10 (d, J=16.2 Hz, 1H), 7.00 (d, J=16.2 Hz, 1H).

EXAMPLE 7

General Procedure for Heck Reaction of Deactivated Aryl Bromides and Activated Chlorides with Olefins

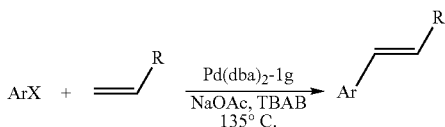

Pd(dba)₂ (1.5 mg, 0.0025 mmol), thiourea 1g (3.4 mg, 0.01 mmol) and sodium acetate (33 mg, 3.8 mmol) were stirred in molten TBAB (0.5 g) for 10 min at 100° C. Aryl halide (0.25 mmol, S/C=100) and olefin (0.38 mmol) were added in turn. Then the flask was sealed with a septa and heated at 135° C. After indicated time, the solution was dilute with ethyl acetate (20 mL) and washed with water and brine. Ethyl acetate was removed under vacuum and nitrobenzene (0.0128 mL) was added as internal standard. The yield of coupling product was determined by ¹H NMR (400 MHz or 300 MHz) analysis, by comparing the peak intensities of the α/β-H of the product and the ortho-H of nitrobenzene (internal standard).

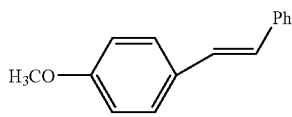

¹H NMR (400 MHz, CDCl₃) δ 7.64-7.52 (m, 4H), 7.45-7.40 (m, 3H), 7.33 (d, J=12.1 Hz, 1H), 7.10 (d, J=12.1 Hz, 1H), 6.98 (d, J=8.2 Hz, 2H), 3.88 (s, 3H).

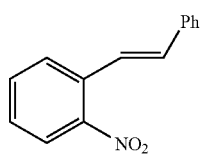

¹H NMR (400 MHz, CDCl₃) δ 7.93 (d, J=7.0 Hz, 1H), 7.74 (d, J=7.0 Hz, 1H), 7.60-7.51 (m, 5H), 7.39-7.30 (m, 3H), 7.07 (d, J=16.1 Hz, 1H).

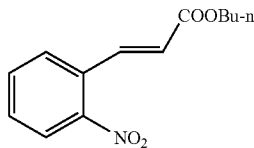

¹H NMR (400 MHz, CDCl₃) δ 8.13 (d, J=17.3 Hz, 1H), 8.05 (d, J=7.8 Hz, 1H), 7.84 (d, J=6.8 Hz, 1H), 7.27-7.24 (m, 2H), 6.36 (d, J=17.3 Hz, 1H), 4.22 (t, J=5.0 Hz, 2H), 1.71-1.67 (m, 2H), 1.32-1.28 (m, 2H), 0.96 (t, J=6.8 Hz, 3H).

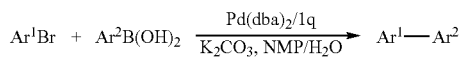

¹H NMR (300 MHz, CDCl₃) δ 7.62 (d, J=15.6 Hz, 1H), 7.41 (d, J=7.1 Hz, 2H), 6.66 (d, J=7.1 Hz, 2H), 6.22 (d, J=15.6 Hz, 1H), 4.18 (t, J=6.7 Hz, 2H), 3.00 (s, 6H), 1.71-1.66 (m, 2H), 1.47-1.40 (m, 2H), 0.96 (t, J=8.2 Hz, 3H).

EXAMPLE 8

General Procedure for the Suzuki Reaction of Aryl Halides with Boric Acids

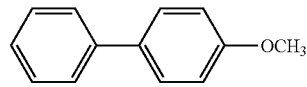

Aryliodide or bromide (0.5 mmol), arylboric acid (0.6 mmol), K₂CO₃ (1.0 mmol), bis-thiourea-Pd(dba)₂ 1q complex in NMP (2.5×10⁻³ M solution) and NMP/H₂O (0.75 ml/0.25 ml) were added to a flask under aerobic conditions. The flask was sealed with rubber septa and heated at the desired temperature. The reaction mixture was diluted with ethyl acetate, washed with brine, and dried over Na₂SO₄. The solvent was removed and the residue was purified by a flash chromatography on silica gel to give the product.

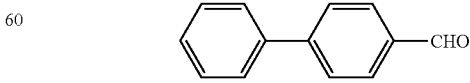

¹H NMR (200 MHz, CDCl₃) δ 7.56-7.50 (m, 4H), 7.44-7.37 (m, 2H), 7.32-7.25 (m, 1H), 6.97 (d, J=8.7 Hz, 2H), 3.84 (s, 3H).

¹H NMR (200 MHz, CDCl₃) δ 10.05 (s, 1H), 7.97-7.93 (m, 2H), 7.77-7.72 (m, 2H), 7.66-7.61 (m, 2H), 7.52-7.39 (m, 3H).

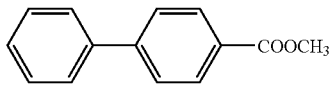

¹HNMR (200 MHz, CDCl₃) δ 8.10 (d, J=8.2 Hz, 2H), 7.68-7.60 (m, 4H), 7.49-7.36 (m, 3H), 3.93 (s, 3H).

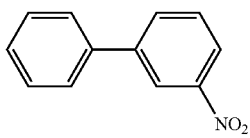

¹H NMR (200 MHz, CDCl₃) δ 8.45 (m, 1H), 8.21-8.17 (m, 1H), 7.93-7.89 (m, 1H), 7.64-7.56 (m, 3H), 7.50-7.42 (m, 3H).

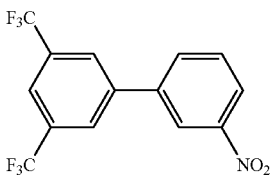

¹H NMR (400 MHz, CDCl₃) δ 8.50-8.49 (m, 1H), 8.34 (d, J=8.0 Hz, 1H), 8.06 (s, 2H), 7.98-7.95 (m, 2H), 7.73 (t, J=8.0 Hz, 1H).

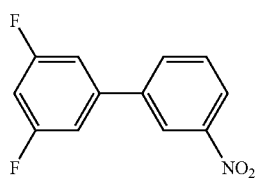

¹H NMR (200 MHz, CDCl₃) δ 8.41-8.40 (m, 1H), 8.28-8.23 (m, 1H), 7.89-7.84 (m, 1H), 7.68-7.60 (m, 1H), 7.16-7.12 (m, 2H), 6.92-6.83 (m, 1H).

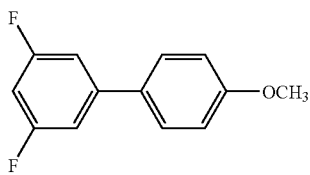

¹HNMR (400 MHz, CDCl₃) δ 7.49 (d, J=8.8 Hz, 2H), 7.09-7.03 (m, 2H), 6.98 (d, J=8.8 Hz, 2H), 6.76-6.70 (m, 1H), 3.86 (s, 3H).

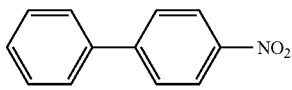

¹H NMR (200 MHz, CDCl₃) δ 8.29 (d, J=9.0 Hz, 2H), 7.73 (d, J=9.0 Hz, 2H), 7.60 (m, 2H), 7.52-7.40 (m, 3H).

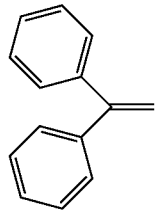

¹HNMR (400 MHz, CDCl₃) δ 7.36-7.33 (m, 10H), 5.47 (s, 2H).

Notes

The following notes correspond to the superscripts contained in the application. Each of the references listed below are incorporated by reference herein.

(1) (a) Heck, R. F. *Acc. Chem. Res.* 1979, 12, 146. (b) De Meijere, A.; Meyer, F. E. *Angew. Chem., Int. Ed.* 1994, 33, 2379. (c) Cabri, W.; Candiani, 1. *Acc. Chem. Res.* 1995, 28, 2. (d) Negishi, E.; Coperet, C.; Ma, S.; Liou, S.; Liu, F. *Chem. Rev.* 1996, 96, 365. (e) Crisp, G. T. *Chem. Soc. Rev.* 1998, 27, 427. (f) Beletskaya, I. P.; Cheprakov, A. V. *Chem. Rev.* 2000, 100, 3009. (g) Whitcombe, N. J.; Kuok Hii, K.; Gibson, S. E. *Tetrahedron* 2001, 57, 7449. (h) Dounay, A. B.; Overman, L. E. *Chem Rev.* 2003, 103, 2945

(2) (a) Littke, A. F.; Fu, G. C. *J. Org. Chem.* 1999, 64, 10. (b) Littke, A. F.; Fu, G. C. *J. Am. Chem. Soc.* 2001, 123, 6989. (c) Shaughnessy, K. H.; Kim, P.; Hartwig, J. F. *J. Am. Chem. Soc.* 1999, 121, 2123. (d) Stambuli, J. P.; Stauffer, S. R.; Shaughnessy, K. H.; Hartwig, J. F. *J. Am. Chem. Soc.* 1999, 121, 2677. (e) Ehrentraut, A.; Zapf, A.; Beller, M. Synlett 2000, 1589.

(3) (a) Ben-David, Y.; Portnoy, M.; Gozin, M., Milstein, D. *Organometallics* 1992, 11, 1995. (b) Portnoy, M.; Milstein, D. *Organometallics* 1993, 12, 1655. (c) Portnoy, M.; Ben-David, Y.; Milstein, D. *Organometallics* 1993, 12, 4734. (d) Portnoy, M.; Ben-Dvid, Y.; Rousso, I.; Milstein, D. *Organometallics* 1994, 13, 3465. (e) Shaw, B. L.; Perera, S. D. *Chem. Commun.* 1998, 1863.

(4) For recent reviews on palladacycles for Heck reactions, see: (a) Dupont, J.; Pfeffer, M.; Spencer, *J. Eur. J. Inorg. Chem.* 2001, 1917. (b) Benford, R. B. *Chem. Commun.* 2003, 1787.

(5) For the use of tetraphenylphosphonium salts in Heck reactions, see: Reetz, M. T.; Lohmer, G.; Schwickardi, R. *Angew. Chem., Int. Ed.,* 1998, 37, 481.

(6) For phosphorus-free palladacycles as catalysts, see Ref. 4.

(7) For recent reviews on N-heterocyclic carbene-palladium catalysts, see: (a) Herrmann, W. A. *Angew. Chem., Int Ed.* 2002, 41, 1290. (b) Yong, B. S.; Nolan, S. P. *Chemtracts-Organic Chemistry* 2003, 205.

(8) For recent reports on Heck reactions using catalysts that are air and moisture stable, see: (a) Buchmeiser, M. R.; Wurst, K. *J. Am. Chem. Soc.* 1999, 121, 11101. (b) Silberg, J.; Schareina, T.; Kempe, R.; Wurst, K.; Buchmeiser, M. R. *J. Organomet. Chem.* 2001, 622, 6. (c) Masliorens, J.; Moreno-Manas, M.; Pla-Quintana, A.; Roglans, A. *Org. Lett.* 2003, 5, 1559.

(9) (a) Touchard, F.; Fache, F.; Lemaire, M. *Tetrahedron: Asymmetry* 1997, 8, 3319. (b) Touchard, F.; Gamez, P.; Fache, F.; Lemaire, M. *Tetrahedron Lett.* 1997, 38, 2275. (c) Touchard, F.; Bernard, M.; Fache, F.; Delbecq, F.; Guiral, V.; Sautet, P.; Lemaire, M. *J. Organomet. Chem.* 1998, 567, 133. (d) Tommasino, M. L.; Casalta, M.; Breuzard, J. A. J.; Lemaire, M. *Tetrahedron: Asymmetry* 2000, 11, 4835. (e) Breuzard, J. A. J.; Tommasino, M. L.; Touchard, F.; Lemaire, M.; Bonnet, M. C. *J. Mol. Catal. A: Chem.* 2000, 156, 223. (f Touchard, F.; Bernard, M.; Fache, F.; Lemaire, M. *J. Mol. Catal. A: Chem.* 1999, 140, 1.

(10) (a) De Munno, G.; Gabriele, B.; Salerno, G. *Inorg. Chim. Acta* 1995, 234, 181. (b) Gabriele, B.; Salerno, G.; Costa, M.; Chiusoli, G. P. *J. Organomet. Chem.* 1995, 503, 21. (c) Zhang, T. Y.; Allen, M. J. *Tetrahedron Lett.* 1999, 40, 5813. (d) Nan, Y.; Miao, H.; Yang, Z. *Org. Lett.* 2000, 2, 297. (e) Miao, H.; Yang, Z. *Org. Lett.* 2000, 2, 1765. (f) Hu, Y.; Yang, Z. *Org. Lett.* 2001, 3, 1387.

(11) Dai, M.; Liang, B.; Wang, C.; Chen, J.; Yang, Z. *Org. Lett.* 2004, 6, 221.

(12) Gurtler, C.; Buchwald, S. L. *Chem. Eur. J.* 1999, 5, 3107 and references therein.

(13) Selvakumar, K.; Zapf, A.; Beller, M. *Org. Lett.* 2002, 4, 3031.

(14) For recent reviews on the use of ionic liquids as solvents, see: (a) Olivier-Bourbigou, H.; Magna, L. *J. Mol. Catal. A: Chem.* 2002, 182-183, 419. (b) Dupont, J.; de Souza, R. F.; Suarez, P. A. Z. *Chem. Rev.* 2002, 102, 3667. (c) Davis, J. H. Jr.; Fox, P. A. *Chem. Commun.* 2003, 1209.

(15) For recent reviews on Suzuki coupling, see: (a) Hassan, J.; Sévignon, M.; Gozzi, C.; Schulz, E.; Lemaire, M. *Chem. Rev.* 2002, 102, 1359. (b) Miura, M. *Angew. Chem. Int. Ed.* 2004, 43, 2201.

(16) (a) Darses, S.; Michaud, G.; Genet, J.-P. *Eur. J. Org. Chem.* 1999, 1875; (b) Molander, G. A.; Katona, B. W.; Machrouhi, F. *J. Org. Chem.* 2002, 67, 8416. (b) Darses, S. Genet, J.-P. *Eur. J. Org. Chem.* 2003, 4313.

We claim:

1. An N,N'-disubstituted thiourea ligand represented by structure I:

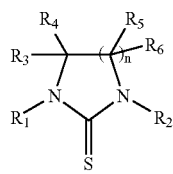

wherein n is an integer in the range of 1 to 8 inclusive;

$R_1$ and $R_2$ are independently for each occurrence cycloalkyl, aryl, aralkyl, or —$(CH_2)_m$—$R_{80}$;

$R_3$, $R_4$, $R_5$, and $R_6$ are independently for each occurrence H, alkyl, halogenated alkyl, cycloalkyl, aryl, aralkyl, —$(CH_2)_m$—$R_{80}$, $COOR_v$ (where $R_v$=alkyl, cycloalkyl, aryl, aralkyl, and —$(CH_2)_m$—$R_{80}$), and $CONR_uR_v$ (where $R_u$ or $R_v$=H, alkyl, cycloalkyl, aryl, aralkyl, and —$(CH_2)_m$—$R_{80}$);

$R_{80}$ represents unsubstituted or substituted aryl, cycloalkyl, cycloalkenyl, or another polycycle;

m is independently for each occurrence an integer in the range of 0 to 8 inclusive; and the N,N'-disubstituted thiourea ligand, when chiral, is a mixture of enantiomers or a single enantiomer.

2. The N,N'-disubstituted thiourea ligand of claim 1, wherein:

$R_1$ and $R_2$ are independently for each occurrence 2,4,6-mesityl, 2,5-di-t-butylphenyl, 2,6-diethylphenyl or t-butyl;

$R_3$, $R_4$, $R_5$, and $R_6$ are absent;

and n=1 and 2.

3. An N,N'-disubstituted thiourea ligand represented by structure II:

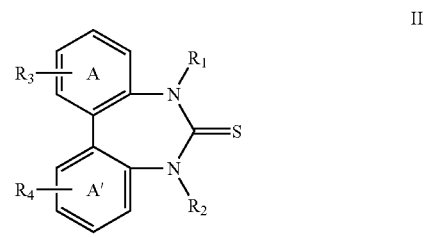

wherein $R_1$ and $R_2$ are independently for each occurrence alkyl, cycloalkyl, aryl, aralkyl, or —$(CH_2)_m$—$R_{80}$;

the A and A' rings of the biphenyl core independently are unsubstituted or substituted with $R_3$ and $R_4$, respectively, one, two, three, or four times;

$R_3$ and $R_4$ are independently for each occurrence H, alkyl, cycloalkyl, aryl, aralkyl, halogen, alkoxyl, —$SiR_3$, or —$(CH_2)_m$—$R_{80}$;

$R_{80}$ represents unsubstituted or substituted aryl, cycloalkyl, cycloalkenyl, or another polycycle;

m is independently for each occurrence an integer in the range of 0 to 8 inclusive; and the N,N'-disubstituted thiourea ligand, when chiral, is a mixture of enantiomers or a single enantiomer.

4. The N,N'-disubstituted thiourea ligand of claim 3, wherein:

$R_3$ and $R_4$ are absent, and $R_1$ and $R_2$ are independently for each occurrence benzyl, 2,4,6-trimethylbenzyl, cyclohexyl or isopropyl.

5. The N,N'-disubstituted thiourea ligand of claim 3, wherein:

$R_3$ and $R_4$ are methyl or methoxy, and $R_1$ and $R_2$ are independently for each occurrence benzyl, 2,4,6-trimethylbenzyl, cyclohexyl or isopropyl.

6. An N,N'-disubstituted thiourea ligand represented by structure III:

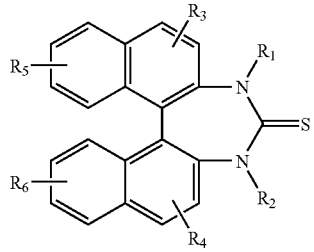

wherein $R_1$ and $R_2$ are independently for each occurrence alkyl, cycloalkyl, aryl, aralkyl, or —$(CH_2)_m$—$R_{80}$;

the four aryl rings of the binaphthyl core independently are unsubstituted or substituted with $R_3$, $R_4$, $R_5$, and $R_6$, respectively, any number of times up to the limitations imposed by stability and rules of valence;

$R_3$, $R_4$, $R_5$, and $R_6$ are independently for each occurrence H, alkyl, cycloalkyl, aryl, aralkyl, halogen, alkoxyl, —$SiR_3$, or —$(CH_2)_m$—$R_{80}$;

$R_{80}$ represents unsubstituted or substituted aryl, cycloalkyl, cycloalkenyl, or another polycycle;

m is independently for each occurrence an integer in the range of 0 to 8 inclusive; and the N,N'-disubstituted thiourea ligand, when chiral, is a mixture of enantiomers or a single enantiomer.

7. The N,N'-disubstituted thiourea ligand of claim 6, wherein:

$R_3$, $R_4$, $R_5$, and $R_6$ are absent;

$R_1$ and $R_2$ are preferentially selected, independently for each occurrence, from benzyl, 2,4,6-trimethylbenzyl, cyclohexyl and isopropyl.

8. The N,N disubstituted thiorarea ligand of claim 1, wherein N is an integer between 1 and 8 inclusive; and $R_1$ and $R_2$ are independently for each occurrence aryl.

* * * * *